US011322299B2

(12) United States Patent
Walser

(10) Patent No.: US 11,322,299 B2
(45) Date of Patent: May 3, 2022

(54) FOLDED MRI SAFE COIL ASSEMBLY

(71) Applicant: DePuy Synthes Products, Inc., Raynham, MA (US)

(72) Inventor: Jochen Walser, Ostermundigen (CH)

(73) Assignee: DePuy Synthes Products, Inc., Raynham, MA (US)

( * ) Notice: Subject to any disclaimer, the term of this patent is extended or adjusted under 35 U.S.C. 154(b) by 588 days.

(21) Appl. No.: 16/052,685

(22) Filed: Aug. 2, 2018

(65) Prior Publication Data

US 2019/0043663 A1 Feb. 7, 2019

Related U.S. Application Data

(60) Provisional application No. 62/541,985, filed on Aug. 7, 2017.

(51) Int. Cl.
*H01F 27/40* (2006.01)
*H01F 17/00* (2006.01)
(Continued)

(52) U.S. Cl.
CPC ......... *H01F 27/402* (2013.01); *A61B 5/0031* (2013.01); *A61B 5/055* (2013.01);
(Continued)

(58) Field of Classification Search
CPC .. H01F 27/402; H01F 17/0006; H01F 41/041; H01F 2017/0073; A61B 5/0031;
(Continued)

(56) References Cited

U.S. PATENT DOCUMENTS 2,834,855 A * 5/1958 Carpenter .............. H01H 9/102
218/43
3,123,692 A * 3/1964 Weber .................... H01H 9/104
337/149

(Continued)

FOREIGN PATENT DOCUMENTS

FR 2625604 A1 7/1989

OTHER PUBLICATIONS

Carpi F et al: "Silicone made contractile dielectric elastomer actuators inside 3-Tesla MRI environment", Intelligent Robots and Systems, 2008. IROS 2008. IEEE/RSJ International Conference on, IEEE, Piscataway, NJ, USA, Sep. 22, 2008 (Sep. 22, 2008), pp. 137-142.

*Primary Examiner* — Anatoly Vortman
(74) *Attorney, Agent, or Firm* — BakerHostetler

(57) ABSTRACT

Implants or sensors often include and rely on inductive and ferromagnetic electrical components to measure and communicate data outside of the body to an external device, creating a safety concern when a patient with these implants or sensors must undergo an MRI scan. Further, various external devices that include inductive and ferromagnetic electrical components are exposed to potentially damaging MRI scans. An electrical coil assembly can include an electrical coil that includes a substrate and an electrical conductor supported by a first face of the substrate. In an example, the electrical coil assembly further includes a fuse element that is configured to move from a disengaged position in which the electrical fuse conductor is out of contact with the electrical conductor to an engaged position in which the electrical fuse conductor contacts the electrical conductor so as to define a short circuit.

14 Claims, 9 Drawing Sheets

(51) Int. Cl.
*H01F 41/04* (2006.01)
*A61B 5/00* (2006.01)
*A61B 5/055* (2006.01)
*H01H 31/12* (2006.01)
*H01H 85/046* (2006.01)
*H01H 85/54* (2006.01)
*G01R 33/28* (2006.01)
*A61B 5/07* (2006.01)
*A61B 5/01* (2006.01)
*A61B 5/145* (2006.01)
*A61B 5/1455* (2006.01)

(52) U.S. Cl.
CPC ....... *A61B 5/6878* (2013.01); *H01F 17/0006* (2013.01); *H01F 41/041* (2013.01); *H01H 31/12* (2013.01); *H01H 31/122* (2013.01); *H01H 85/046* (2013.01); *H01H 85/54* (2013.01); *A61B 5/0008* (2013.01); *A61B 5/01* (2013.01); *A61B 5/076* (2013.01); *A61B 5/14539* (2013.01); *A61B 5/14552* (2013.01); *A61B 5/4851* (2013.01); *A61B 2562/0247* (2013.01); *A61B 2562/0261* (2013.01); *A61B 2562/12* (2013.01); *G01R 33/288* (2013.01); *H01F 2017/0073* (2013.01)

(58) Field of Classification Search
CPC ..... A61B 5/055; A61B 5/6878; A61B 5/0008; A61B 5/01; A61B 5/076; A61B 5/14539; A61B 5/14552; A61B 5/4851; A61B 2562/0247; A61B 2562/0261; A61B 2562/12; H01H 31/12; H01H 31/122; H01H 85/046; H01H 85/54; G01R 33/288
USPC ........................................................ 337/142
See application file for complete search history.

(56) References Cited

U.S. PATENT DOCUMENTS

| | | | | |
|---|---|---|---|---|
| 4,292,616 | A | * | 9/1981 | Andersen ............. H01H 23/105 337/143 |
| 4,556,874 | A | * | 12/1985 | Becker .................. H02H 3/046 340/638 |
| 5,014,036 | A | * | 5/1991 | Komoto ................ H01H 9/102 337/4 |
| 5,831,507 | A | * | 11/1998 | Kasamatsu ........... H01H 9/102 337/4 |
| 7,570,148 | B2 | | 8/2009 | Parker et al. |
| 8,258,909 | B2 | | 9/2012 | Li et al. |
| 8,649,842 | B2 | | 2/2014 | Atalar et al. |
| 9,263,211 | B2 | * | 2/2016 | Weinreich ................ H01H 3/50 |
| 9,443,683 | B2 | | 9/2016 | Hrnicko et al. |
| 10,276,314 | B2 | * | 4/2019 | Minke ...................... H01H 3/02 |
| 2002/0109574 | A1 | | 8/2002 | Handcock et al. |
| 2003/0210811 | A1 | | 11/2003 | Dubowsky et al. |
| 2007/0062031 | A1 | | 3/2007 | Kamp |
| 2007/0109704 | A1 | * | 5/2007 | Apfelbacher .......... H01H 9/548 361/93.1 |
| 2011/0050226 | A1 | | 3/2011 | Schellekens et al. |

* cited by examiner

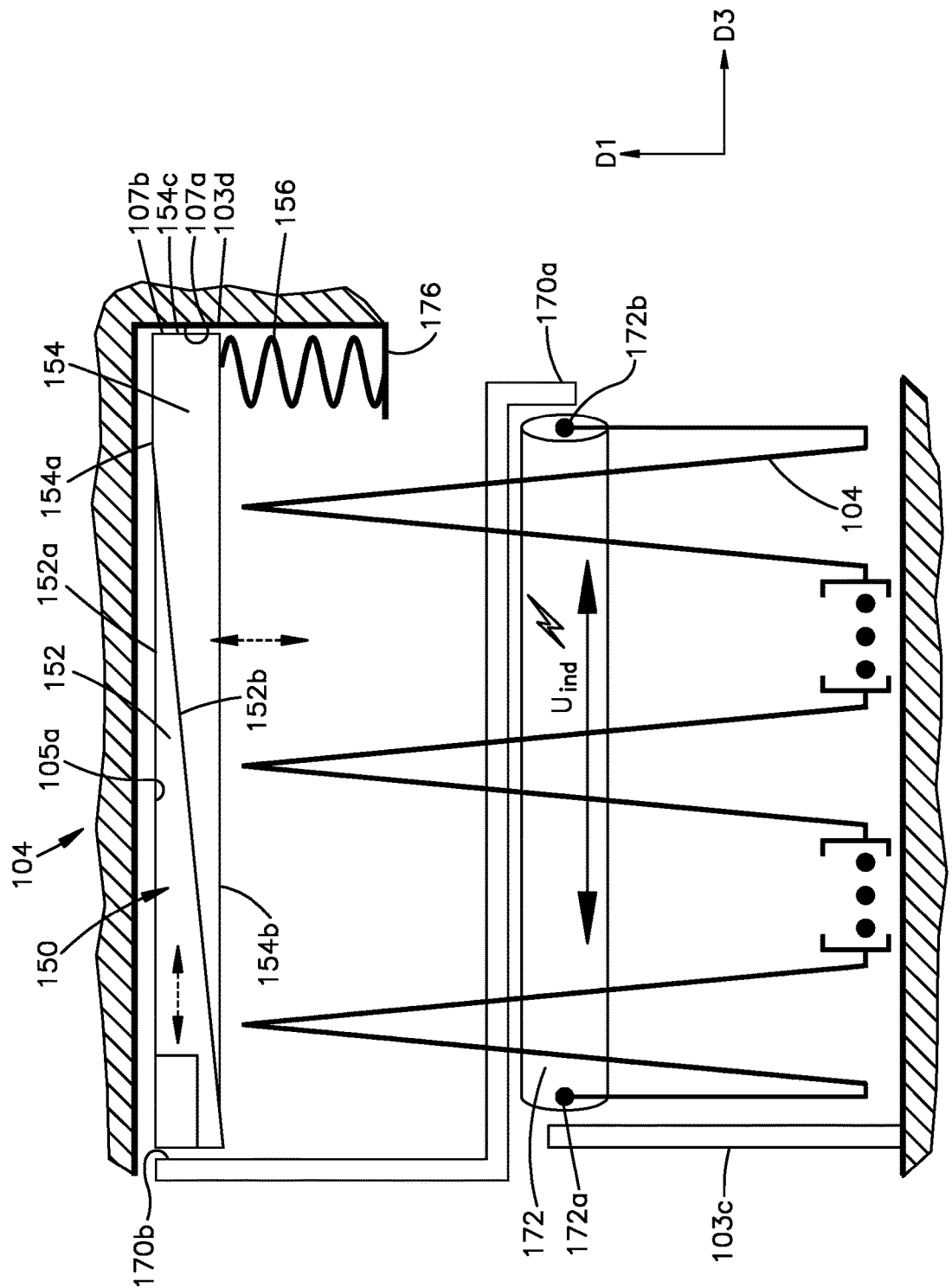

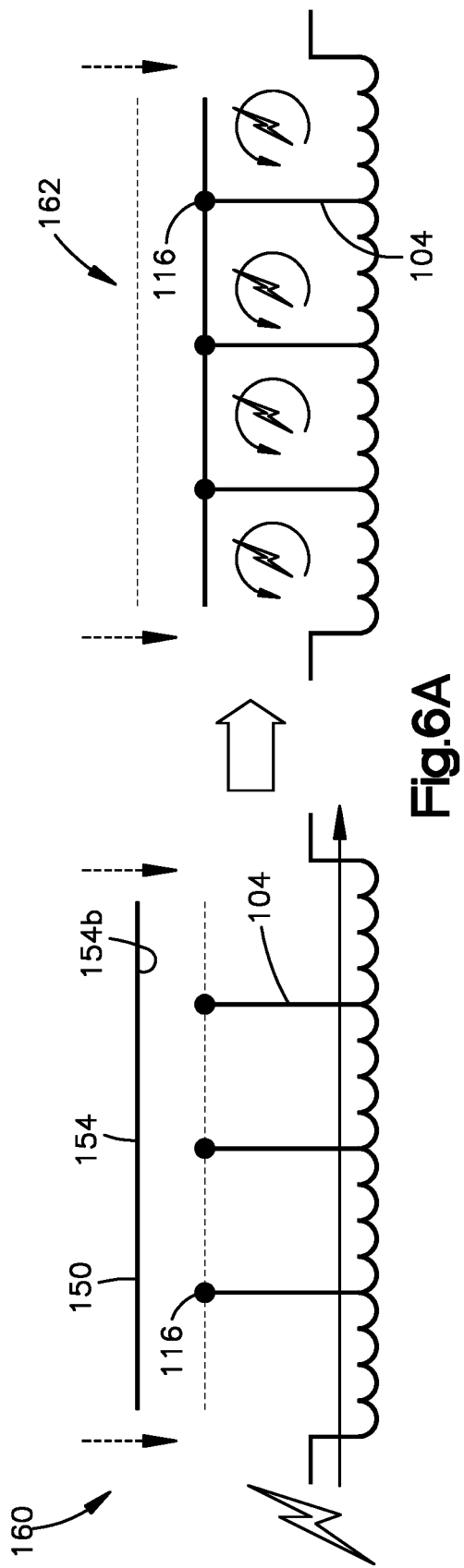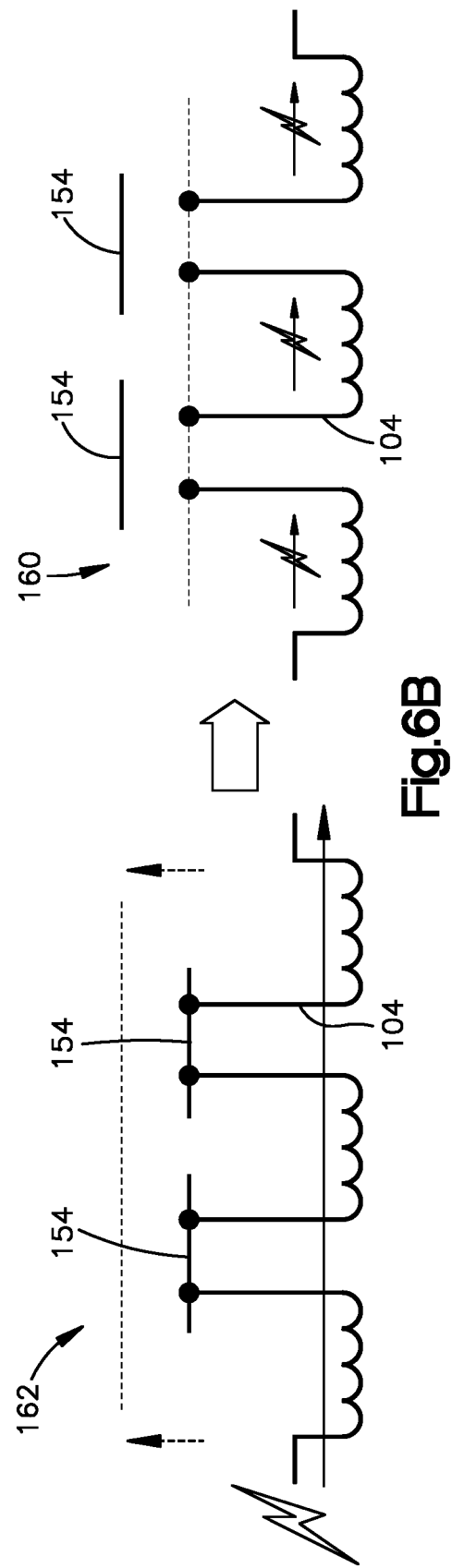

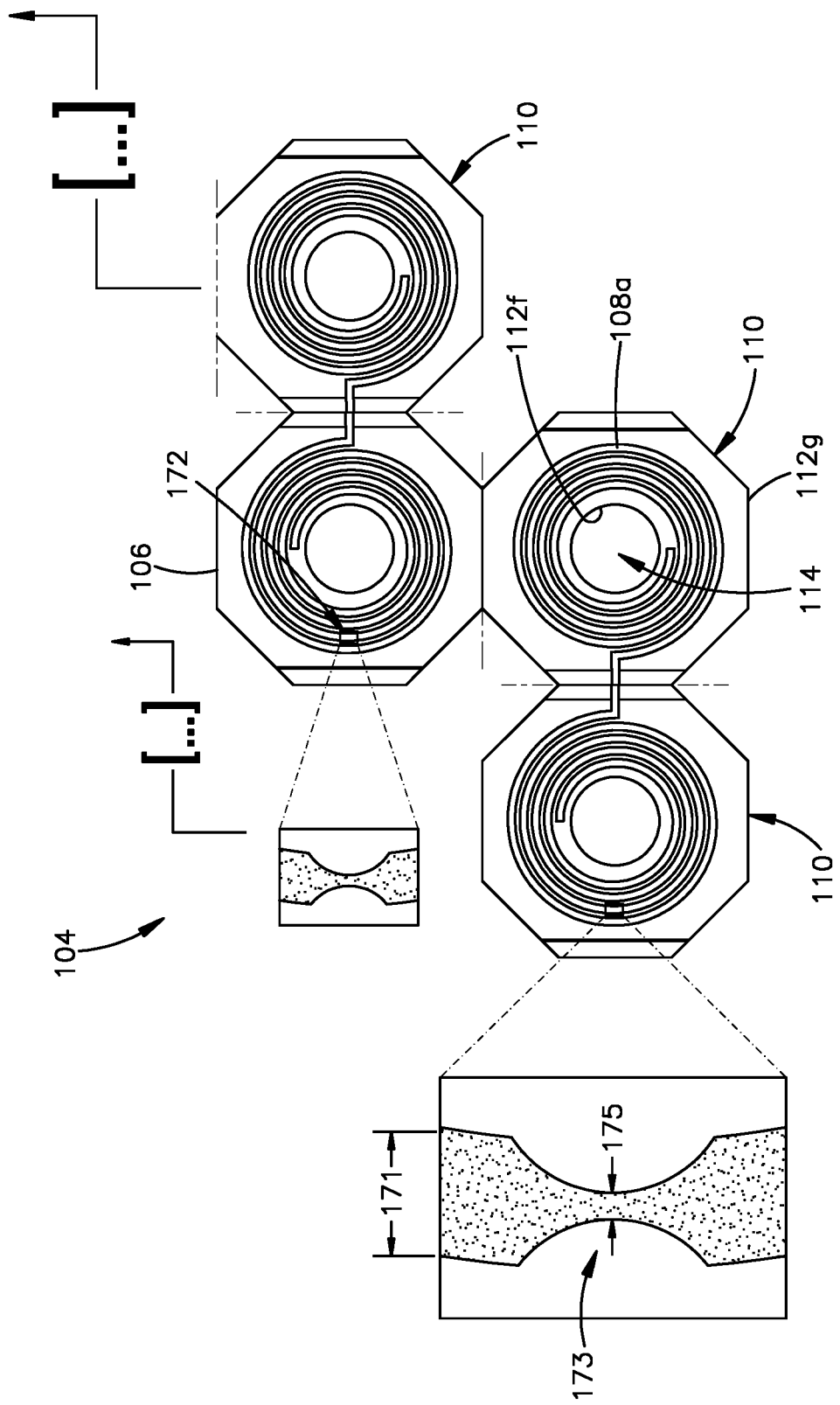

FOLDED MRI SAFE COIL ASSEMBLY

CROSS REFERENCE TO RELATED APPLICATIONS

This Application claims the benefit of U.S. Provisional Patent Application Ser. No. 62/541,985, filed Aug. 7, 2017, the disclosure of which is hereby incorporated by reference as if set forth in its entirety.

TECHNICAL FIELD

The present invention relates to electrical coil assemblies that can prevent the induction of electrical voltages or currents.

BACKGROUND

Magnetic resonance imaging (MRI) is often used to generate pictures of a patient's anatomy, among other uses. To generate the pictures, MRI scanners often emit strong magnetic fields, radio waves, and field gradients. Such emissions can cause damage to inductive and ferromagnetic electrical components, for instance electrical coils and magnets, which are within range of an MRI scanner. By way of example, smart implants or sensors are increasingly implanted into a patient's body to monitor an implant or an aspect of the patient's health over time. These implants or sensors often include and rely on inductive and ferromagnetic electrical components to measure and communicate data outside of the body to an external device, creating a safety concern when a patient with these implants or sensors must undergo an MRI scan. Further, various external devices that include inductive and ferromagnetic electrical components are exposed to potentially damaging MRI scans.

SUMMARY

In one example, an electrical coil assembly includes an electrical coil that includes a substrate and an electrical conductor supported by the substrate, and the electrical coil defines at least two exposed regions. The electrical coil assembly further includes a fuse element including an electrical fuse conductor proximate to the electrical coil. The fuse element can be movable from a disengaged position whereby the electrical fused conductor is spaced from the at least two exposed regions, to an engaged position whereby the electrical fuse conductor is in electrical communication with the at least two exposed regions, such that current flows from a first one of the two exposed regions through the electrical fuse conductor to a second one of the two exposed regions. The electrical coil assembly can be responsive to a magnetic field between approximately 1 Tesla and 5 Tesla so as to urge the fuse element to move from the disengaged position to the engaged position.

In another example, an electrical coil assembly is manufactured by stamping an electrical conductor on a first face of a substrate so as to define an electrical coil. The electrical coil is folded into a folded position so as to define a first plurality of folded edges of the electrical coil. A fuse element is arranged proximate to the first plurality of folded edges, such that the fuse element is spaced from the first plurality of folded edges along the transverse direction, and such that the first face of the substrate faces the fuse element at the first plurality of folded edges, so as to expose the electrical conductor to the fuse element at the first plurality of folded edges.

In another example, an electrical device or a patient is protected when exposed to magnetic resonance imaging, wherein the electrical device or patient includes an electrical coil comprising a substrate and an electrical conductor supported by the substrate. The electrical coil defines at least two exposed regions. A fuse element including an electrical fuse conductor is caused to move from a disengaged position in which the electrical fuse conductor is spaced from the at least two exposed regions to an engaged position in which the electrical fuse conductor is in electrical communication with the at least two regions, such that current flows from a first one of the two exposed regions through the electrical fuse conductor to a second one of the at least two exposed regions.

In yet another example, an electrical coil includes a substrate and an electrical conductor defining a single continuous trace supported by a first face of the substrate. The electrical coil is arranged in a folded position so as to define a first plurality of folded edges and a second plurality of folded edges opposite the first plurality of folded edges along a transverse direction. The electrical conductor defines a first width and a narrow location having a second width that is less than the first width, such that, when voltages or currents above a predetermined threshold are induced within the electrical coil, the electrical conductor breaks at the narrow location so as to no longer define the single continuous trace.

BRIEF DESCRIPTION OF THE DRAWINGS

The foregoing summary, as well as the following detailed description of embodiments of the application, will be better understood when read in conjunction with the appended drawings. For the purposes of illustrating the methods and electrical coils of the present application, there is shown in the drawings representative embodiments. It should be understood, however, that the application is not limited to the precise methods and devices shown. In the drawings:

FIG. 5 is a side view of a portion of the electrical coil assembly shown in FIG. 3 that includes the voltage actuator, showing an induced voltage within the electrical coil in accordance with an example embodiment, wherein the voltage actuator causes the fuse element to move in response to the induced voltage.

FIG. 6A is a schematic diagram showing the fuse element being urged from a first or disengaged position in which the fuse element is out of contact with the electrical conductor of the electrical coil to a second or engaged position in which the fuse element contacts the electrical conductor of the electrical coil.

FIG. 6B is a schematic diagram showing the fuse element being urged from an engaged position in which the fuse element is in contact with the electrical conductor of the electrical coil to a disengaged position in which the fuse element is out of contact with the electrical conductor of the electrical coil.

FIG. 7 shows the electrical coil in an unfolded position, wherein the electrical coil includes an electrical conductor defining at least one narrow location in accordance with another embodiment.

DETAILED DESCRIPTION

Various smart implants that are implanted into a patient's body, among other electrical devices, include electrical circuits and components that can be damaged by MRI scans. In particular, electrical components that are integrated with smart implants can create safety concerns to a patient who undergoes an MRI scan. Such electrical components include electrical coils, which can induce high voltages and electrical currents during an MRI scan. Electrical coils can be included in implantable devices and in other external devices that are in the vicinity of an MRI device. Various electrical coil assemblies described herein can prevent the induction of high voltages or electrical currents.

Figure 1:
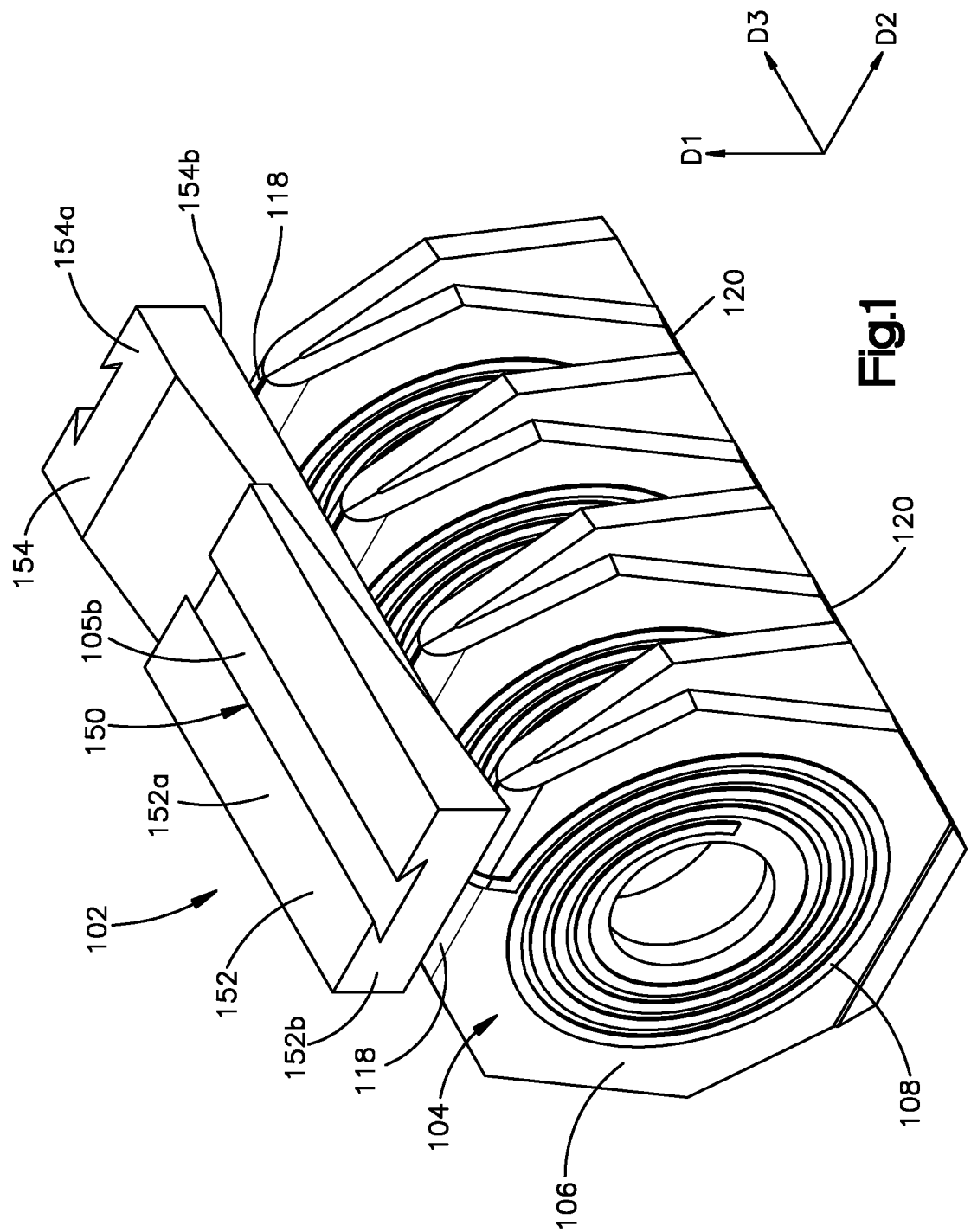
FIG. 1 is a perspective view of an electrical coil assembly including an electrical coil and a fuse element in accordance with an example embodiment.
Figure 2:
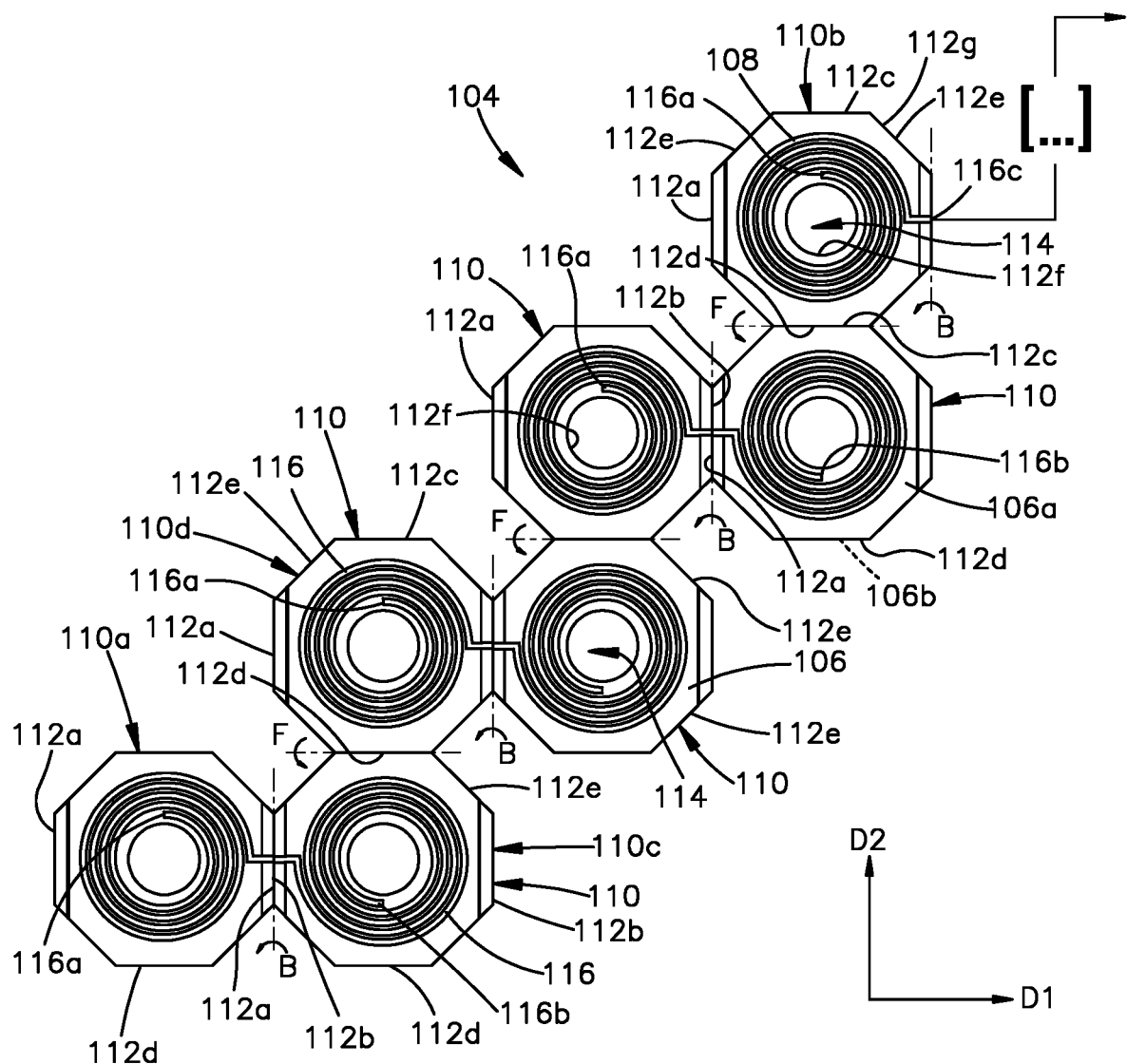
FIG. 2 is a plan view of a portion of the electrical coil shown in FIG. 1, wherein the electrical coil is shown in an unfolded position, and the electrical coil includes an electrical conductor supported by a substrate.

Referring to FIG. 1, an electrical coil assembly 102 can include an electrical coil 104 arranged in a folded position, so as to define a folded electrical coil. It will be understood that FIG. 1 represents a conceptual model, so the folded position and the arrangement of the electrical coil can vary as desired. Referring also to FIG. 2, the electrical coil 104 can include a substrate or film 106 and an electrical conductor 108 supported by the substrate 106. The substrate 106 can include a first or front face 106a and a second or back face 106b opposite the front face 106a. The electrical conductor 108 can be supported by the front face 106a, for instance only the front face 106a, of the substrate 106. The electrical coil 104 can define a plurality of segments 110. Thus, each segment 110 can include a respective portion of the front face 106a and a respective portion of the back face 106b opposite the front face 106a. Further, each segment can include a portion of the electrical conductor 108 arranged on the front face 106a of the substrate 106. The electrical coil can be arranged in the folded position so as to define a first plurality of folded edges 118 and a second plurality of folded edges 120 opposite the first plurality of folded edges 118 along a transverse or first direction D1. The electrical coil can be alternatively arranged (e.g., see FIG. 2) in a folded position so as to define folded edges in any position as desired. For example, the first plurality of folded edges 118 can include edges that are opposite each other, for instance opposite each other along the first direction D1. Similarly, the first plurality of folded edges 118 can include edges oriented, for example, perpendicularly to folded edges in the second plurality of folded edges 120. By way of further example, the second plurality of folded edges 120 can include edges that are opposite each other, for instance opposite each other along the first direction D1.

It is emphasized that FIGS. 1 and 2 depict examples of an electrical coil arrangement and shape to facilitate description of the disclosed subject matter, and are not intended to limit the scope of this disclosure. Thus, the electrical coil can be alternatively arranged (e.g., folded) and shaped in accordance with embodiments disclosed herein, and all such embodiments are contemplated as within the scope of the present disclosure.

Figure 8A:
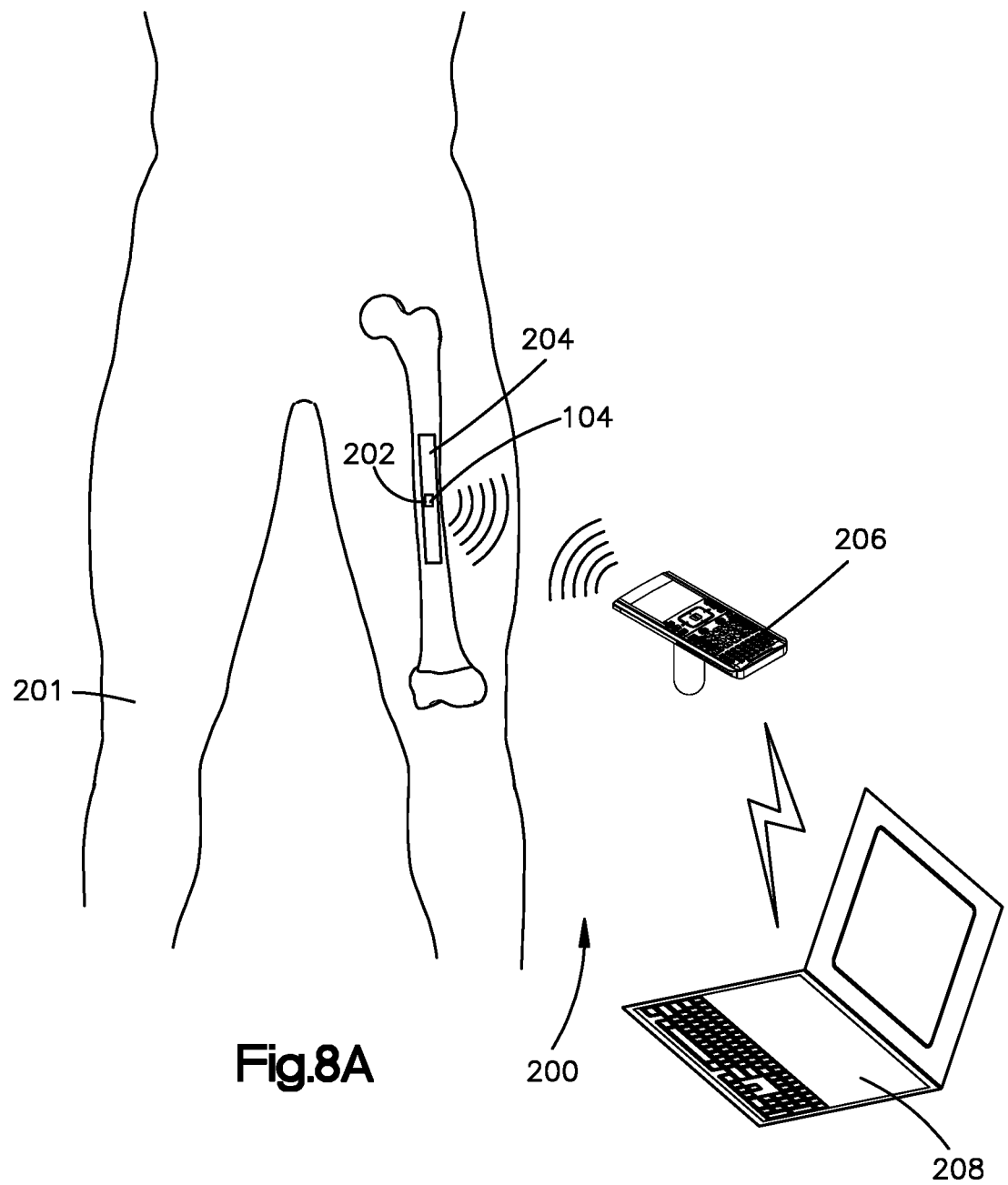
FIG. 8A shows a simplified schematic diagram of a system that measures an anatomical condition of a patient according to one embodiment.

The electrical coil assembly 102 can be configured to be implanted into a patient's body. Referring to FIG. 8A, a system 200 is shown that is configured to track health of a patient over time. In general, the system 200 comprises at least one implantable sensor 202 that is configured to be implanted into a patient's body 201. For example, the electrical coil assembly 102 can be part of an anatomical implant of any suitable type such as (without limitation) a bone plate, an intramedullary nail, a bone anchor, a pedicles screw, a spine rod, an intervertebral implant, and so on. The system can also comprise an anatomical implant 204 configured to support the at least one sensor 202. Alternatively, the electrical coil assembly 102 can be configured to attach directly to an anatomical body of the patient without being supported by an anatomical implant. Alternatively still, the electrical coil assembly 102 can be part of a device that is exposed to magnetic resonance imaging without being implanted. In an example, the electrical coil 104 can be configured as an antenna that converts the measurement value from an electrical signal into radio waves so as to transmit the measurement value wirelessly through the patient's skin to an external wireless communicator situated outside of the patient's body.

The system can further comprise an external wireless communicator 206 configured to wirelessly receive data from the at least one sensor 202 through the skin of the patient when the external wireless communicator 206 is situated outside of the patient's body. The data can then be communicated to a computing device 208 that can be accessed by the patient or a medical professional.

Figure 8B:
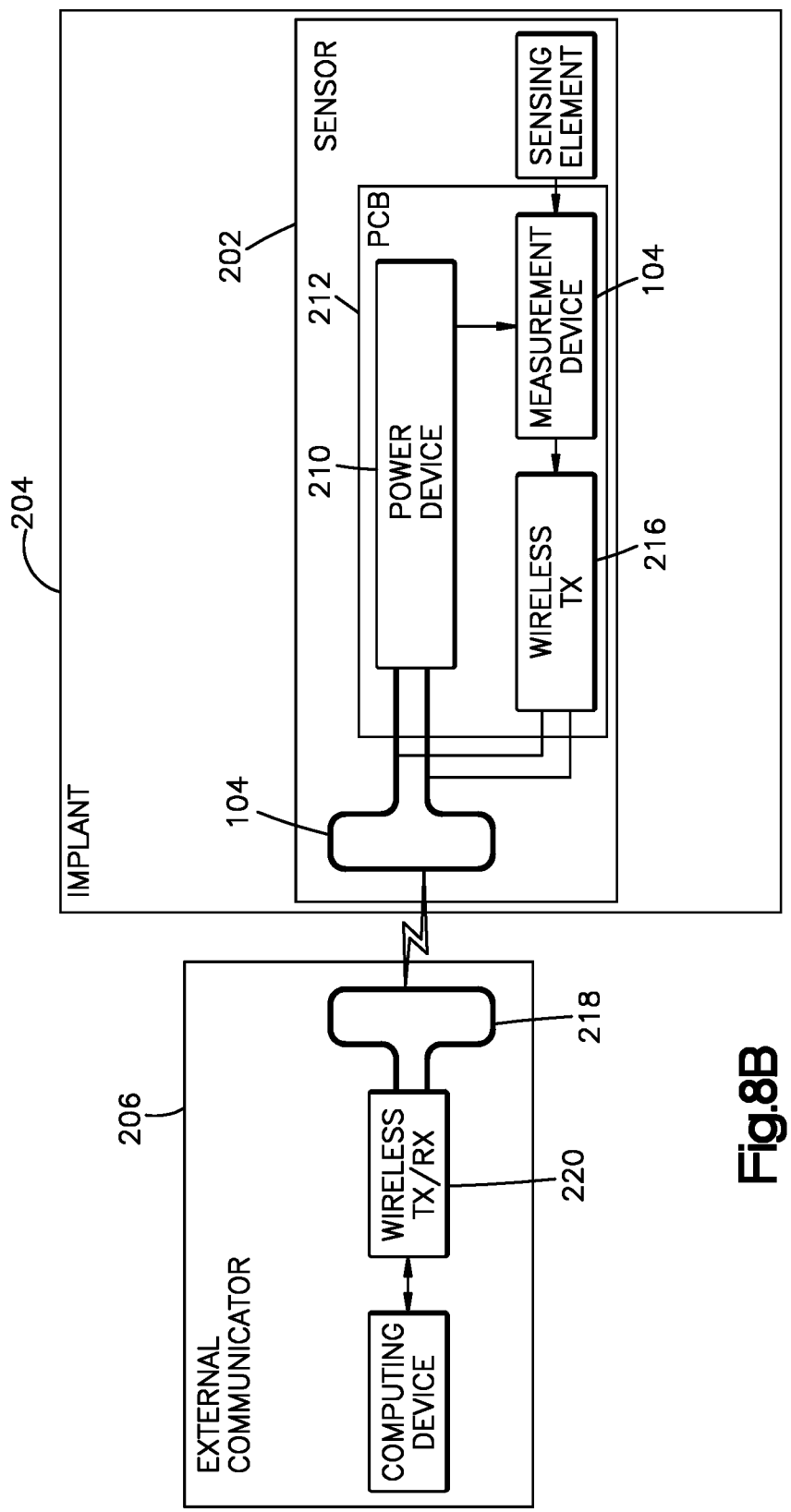
FIG. 8B shows a simplified block diagram of a system that measures an anatomical condition of a patient according to one example.

Referring now to FIG. 8B, the sensor 202 comprises at least one sensing element 218 and a measurement device 214 in communication with the at least one sensing element 218. Together, the at least one sensing element 218 and measurement device 214 are configured to generate a measurement value when the sensor 202 is implanted in the patient's body. The anatomical property can be any suitable property for tracking the health of a patient such as (without limitation) strain, load, deflection, rotation, temperature, pressure, pH level, oxygen level, and so on. The sensor 202 can further comprise an internal wireless communicator in communication with the measurement device 214. The internal wireless communicator is configured to receive the measurement value from the measurement device and wirelessly communicate the measurement value through skin of the patient to the external wireless communicator 206 situated outside of the patient's body. The internal wireless communicator can be configured to communicate wirelessly using passive radio-frequency identification (RFID). Alternatively, the internal wireless communicator can be configured to communicate using any other wireless communication technology suitable for communicating through the skin such as (without limitation) battery-assisted passive RFID, active RFID, blue tooth, and Wi-Fi.

The internal wireless communicator can include a wireless transmitter 216 that receives the measurement value from the measurement device 214 and prepares the measurement value for wireless transmission. For example, the wireless transmitter 216 can include processing such as (without limitation) one or more of (i) memory configured to store the measurement value, (ii) an digital-to-analog converter configured to convert the measurement value to analog format, (iii) a radio frequency (RF) modulator configured to modulate the measurement value, (iv) an errorcorrection encoder configured to encode the measurement value, and other processing consistent with the wireless technology employed by the sensor 202. The wireless transmitter 216 can further include a unique identifier or tag that can be used to distinguish the sensor 202 from other sensors. The wireless communicator can also include the electrical coil assembly 102, which can be configured to convert the measurement value from an electrical signal into radio waves so as to transmit the measurement value wirelessly through the patient's skin to the external wireless communicator 206 situated outside of the patient's body.

The sensor 202 can comprise a power device 210 configured to supply power to the measurement device 214 and wireless communicator. The at least one sensing element 218, printed circuit board 212, and electrical coil assembly 102 can all be supported by the anatomical implant 204, which in turn can be attached to an anatomical body of the patient. Alternatively, the at least one sensing element 218, printed circuit board 212, and electrical coil assembly 102 can all be attached directly to the anatomical body of the patient. The external wireless communicator 206 can include the electrical coil assembly 102 and a wireless transmitter and receiver 220. The wireless transmitter and receiver 220 can be implemented separately or can be implemented as a transceiver. In at least some embodiments, the external wireless communicator 206 can further include a computing device 222. Alternatively, the computing device 222 can be implemented separately from the external wireless communicator 216.

Referring in particular to FIG. 2, each segment 110 of the electrical conductor 108 can include a first edge 112a and a second edge 112b opposite the first edge 112a along the transverse or first direction D1. Each segment 110 of the electrical conductor 108 can further include a third edge 112c and a fourth edge 112d opposite the third edge 112c along a lateral or second direction D2 that is substantially parallel to the first direction D1. Each segment 110 of the electrical conductor 108 can further include a plurality of edges 112e, for instance four edges 112e, that are angularly offset with respect to the first and second directions D1 and D2, respectively. The edges 112e can each extend from an end of the first edge 112a or the second edge 112b, to an end of the third edge 112c or the fourth edge 112d, such that each segment 110 defines an octagon, though it will be understood that the segments 110 can be alternatively shaped as desired. The front and back faces 106a and 106b can extend between the first and second edges 112a and 112b, and between the third and fourth edges 112c and 112d. In the unfolded position depicted in FIG. 2, the front face 106a can be planar along the first and second directions D1 and D2, respectively.

As mentioned above, the illustrated folding pattern is presented to facilitate description of the disclosed subject matter, and is not intended to limit the scope of this disclosure. Thus, the segments 110 can define an octagon or can be alternatively shaped, for instance so as to define a triangle, square, or the like. Further, the alternatively shaped segments may be used to implement embodiments disclosed herein in addition to, or instead of, the illustrated segments, and all such embodiments are contemplated as within the scope of the present disclosure.

Still referring to FIG. 2, each segment 110 can be connected to at least one other segment 110. A first or front segment 110a, in particular the first edge 112a of the front segment 110a, can define a first end of the electrical coil 104 in the unfolded position. A second or rear segment 110b, in particular the third edge 112c of the rear segment 110b, can define a second end of the electrical coil 104 in the unfolded position. Each of the segments 110 can be connected to at least one other segment 110 so as to define the electrical coil 104. In accordance with the illustrated embodiment, the front segment 110a is connected to one other segment 110, the rear segment 110b is connected to one other segment 110, and the other segments 110 are connected to two other segments 110. In particular, the second edge 112b of the front segment 110a is connected to the first edge 112a of a third segment 110c, and the third edge 112c of the third segment 110c is connected to the fourth edge 112d of a fourth segment 110d. Thus, in an example, each of the segments 110, excluding the front segment 110a and the rear segment 110b, can be connected to one segment 110 at either the first edge 112a or the second edge 112b, and one other segment 110 at either the third edge 112c or the fourth edge 112d, so as to define a step pattern depicted in FIG. 2. It will be understood, however, that the segments 110 can be alternatively arranged as desired.

Thus, each segment 110 can include an outer edge 112g that defines an octagon. Each segment 110 can define an inner edge 112f spaced from the outer edge 112g so as to define a hole 114 from the front face 106a of the substrate to the back face 106b of the substrate in each segment 110. As shown, the inner edge 112f is substantially circular, so as define the hole 114 that is substantially circular, but it will be understood that the inner edge 112f, and thus the hole 114, can be alternatively shaped as desired. It will be appreciated that the illustrated electrical coil configuration is presented to facilitate description of the disclosed subject matter, and is not intended to limit the scope of this disclosure. Thus, the holes can define a circle or can be alternatively shaped, for instance so as to define a triangle, square, or the like. Further, the alternatively shaped holes may be used to implement embodiments disclosed herein in addition to, or instead of, the illustrated electrical coils, and all such embodiments are contemplated as within the scope of the present disclosure.

The electrical conductor 108 can include a plurality of conductive wires 116. Each of the conductive wires 116 can include a first or terminal end 116a arranged on one segment 110, and a second end 116b arranged on another segment 110 that is connected to the segment 110 on which the first end 116a is arranged. Each conductive wire 116 can extend about a center of the respective segment 110 in a spiral pattern from the first end 116a to the second end 116b, such that the first end 116a can be spaced from the second end 116b along the first and second directions D1 and D2, respectively. For example, the conductive wire 116 supported by the front segment 110a and the third segment 110c can extend from the first end 116a, about the hole 114 defined by the first segment 110a in a spiral pattern, across the second edge 112b and the first edge 112a of the front segment 110a and the third segment 110c, respectively, and about the hole 114 defined by the third segment 110c to the second end 116b that is spaced from the first end 116a along the second direction D2. The first end 116a can be spaced from the fourth edge 112d a distance along the second direction D2 that is substantially equal to a distance that the second end 116b is spaced from the third edge 112c along the second direction D2. Thus, the first and second ends 116a and 116b can each be spaced equally from a respective center point defined by the respective segments on which each of the ends 116a and 116b is arranged. It will be understood that the electrically wires 116 can define alternative patterns as desired. Further, each of the ends 116a and 116b can be configured as contact pads to electrically connect to an electrical conductor, such as another conductive wire 116. In addition, each of the ends 116a-c can be configured to electrically connect to another segment 110, in accordance with any folded coil configuration desired.

In an example, the electrical coil 104 in the unfolded position is folded into the folded position, such that the first end 116a of a given conductive wire 116 on a given segment 110 is electrically coupled to the second end 116b of the conductive wire 116 on a segment 110 adjacent to the given segment 110. In particular, the third segment 110c can be folded about an axis defined by the second edge 112a of the front segment 110a, such that the back face 106b of the front segment 110a contacts, or is adjacent to, the back face 106b of the third segment 110c. Then the third segment 110c can be folded about an axis defined by the fourth edge 112d of the fourth segment 110d, such that the second end 116b supported by the third segment 110c contacts, and is electrically coupled with, the first end 116a supported by the fourth segment 110d. Folding can proceed in this manner until each of the conductive wires 116 are electrically coupled with each other, such that the electrical conductor 108 defines a single continuous trace in the folded position. In particular, folding can proceed so as to define the electrical conductor 108 that extends from the first end 116a supported by the first segment 110a to a terminal end 116c of the conductor wire 116 supported by the rear segment 110b. Further, each fold at the axis defined by one of the second edges 112a can expose the electrical conductor 108 at the fold so as to define a conductive edge. Each fold at the axis defined by one of the fourth edges 112d can expose no electrical conductor at the fold so as to define a nonconductive edge opposite the conductive edge. Thus, the first plurality of folded edges 118 can include conductive edges and the second plurality of folded edges 120 can include non-conductive edges. Further, the first plurality of folded edges 118 can define at least two exposed regions of the electrical coil 104. In an example, the first end 116a of the front segment 110a is not electrically coupled to another wire 116. Further, the terminal end 116c can be configured so as to not be electrically coupled to one of the wires 116.

Referring again to FIG. 1, in the folded position, each of the segments 110 can be spaced from each other along a longitudinal or third direction D3 that is substantially perpendicular to both the first and second directions D1 and D2, respectively. Thus, the electrical coil 104 arranged in the folded position can define the plurality of segments 110 along the third direction D3, such that each segment 110 is attached to at least one other segment 110 at a folded edge of the first or second plurality of folded edges 118 and 120, respectively. The electrical coil assembly 102 can further include a fuse element 150 that is spaced from the electrical coil 104 along the first direction D1. The fuse element 150 can be proximate to the first plurality of folded edges 118. The fuse element 150 can be spaced from the first plurality of folded edges 118 along the first direction D1. The fuse element 150 can be disposed closer to the first plurality of folded edges 118 as compared to the second plurality of folded edges 120. The front face 106a of the substrate 106 can face the fuse element 150 at the first plurality of folded edges 118, so as to expose the electrical conductor 108 to the fuse element 150 at the first plurality of folded edges 118. The back face 106b of the substrate 106 can face inward at the first plurality of folded edges 118, and the back face 106b face of the substrate 106 can face outward at the second plurality of folded edges 120.

The electrical coil assembly 102 can further include a housing 103 that includes a first end 103a and a second end 103b opposite the first end along the first direction D1. The first end 103a can support the fuse element 150 and the second end can support the electrical coil 104. The housing 103 can further include a third end 103c and a fourth end 103d opposite the third end 103c along the third direction D3.

Figure 3:
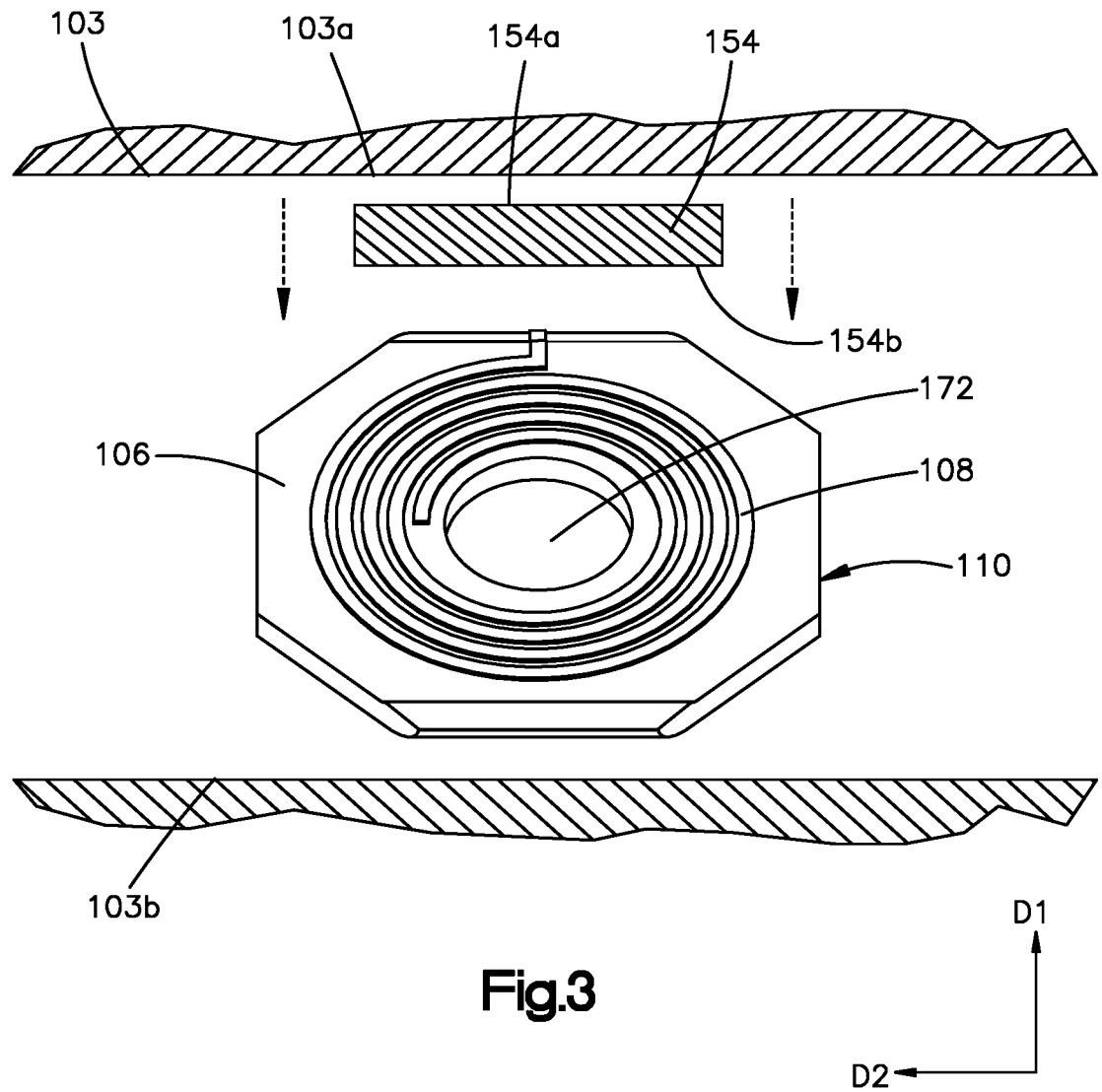
FIG. 3 is a plan view of a segment of the electrical coil assembly shown in FIG. 1, wherein the fuse element further includes a voltage actuator in accordance with an example embodiment.
Figure 4:
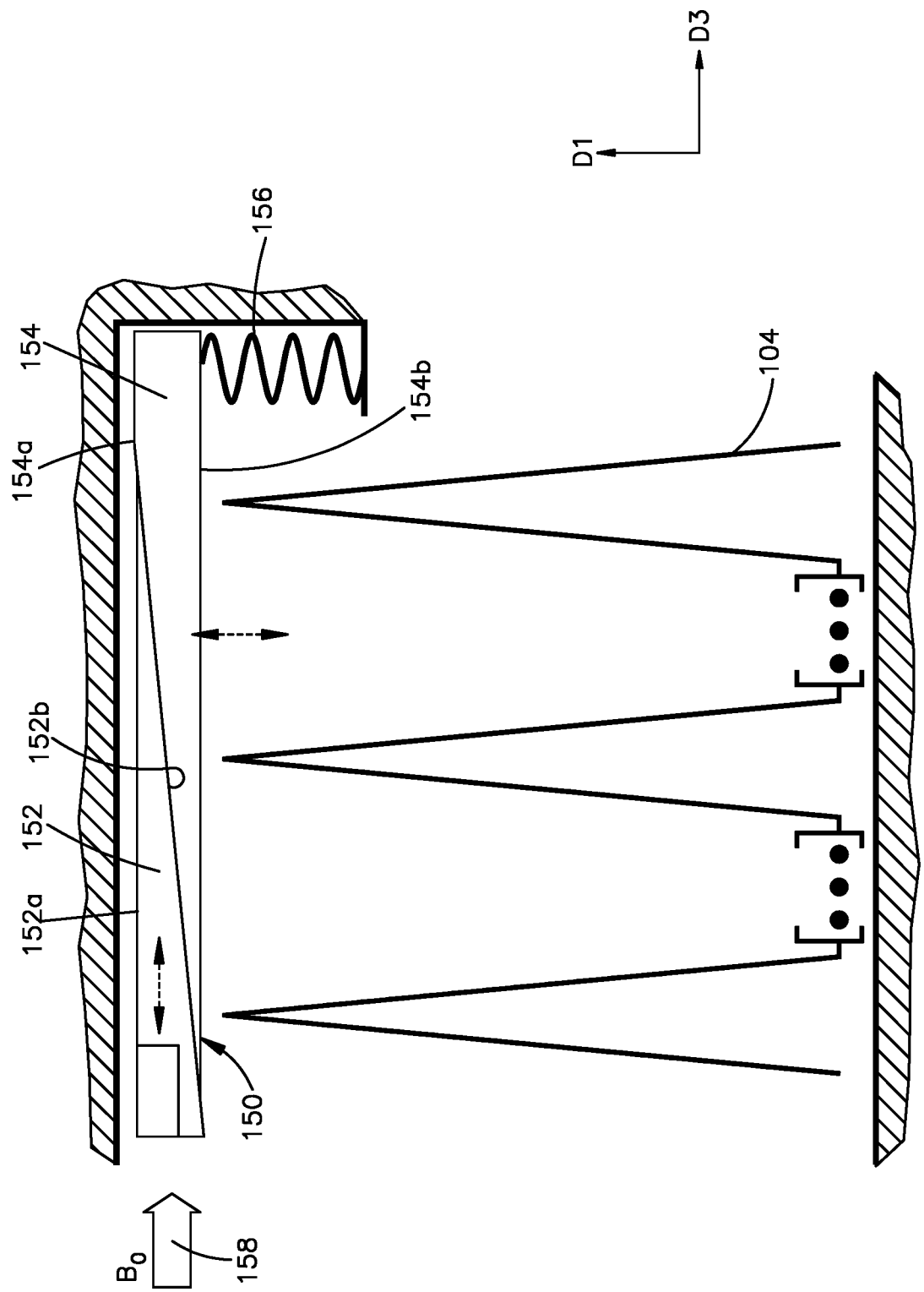
FIG. 4 is a side view of a portion of the electrical coil assembly shown in FIG. 1, wherein the fuse element further includes a magnetic actuator in accordance with an example embodiment.

Referring also to FIGS. 3 to 5, the fuse element 150 can include an actuator 152, for instance a voltage actuator or a magnetic actuator, and an electrical fuse conductor 154 adjacent to the actuator 152. In an example, the electrical fuse conductor 154 is a conductive element that can consist of any electrically conductive material as desired, and the actuator 152 is a nonconductive element that can consist of any insulative material as desired. In another example, the electrical fuse conductor can consist of a housing and an electrically conductive trace supported by the housing. The electrical fuse conductor 154, and thus the electrical coil assembly 102, can be responsive to a magnetic field between approximately 1 Tesla and 5 Tesla, so as to urge the electrical fuse conductor to move toward the first plurality of folded edges 118. Thus, the electrical coil assembly can be responsive to strength levels of conventional MRI machines, for instance 1.5 Tesla and 3.0 Tesla. In particular, in accordance with one example, the actuator 152 can be arranged to move along the third direction D3 when the electrical coil assembly 102 is exposed to the magnetic field or the electrical potential induced in the coil by an MRI machine, so as to cause the electrical fuse conductor 154 to move toward the first plurality of folded edges 118.

The actuator 152 can define a first or top surface 152a and a second or bottom surface 152b opposite the top surface 152a along the first direction D1. The electrical fuse conductor 154 can define a top surface 154a and a bottom surface 154b opposite the top surface 154a along the transverse direction. The bottom surface 152b of the actuator 152 can be configured to ride along the top surface 154a of the electrical fuse conductor 154 when the electrical coil assembly 102 is exposed to a magnetic field, which can be static or dynamic. In an example, the bottom surface 154b of the electrical fuse conductor 154 comprises electrically conductive material. In one example, only the bottom surface 154b of the electrical fuse conductor 154 comprises electrically conductive material. In another example, the electrical fuse conductor 154 is composed entirely of electrically conductive material, though it will be understood the composition of the electrical fuse conductor can vary as desired.

The first end 103a of the housing 103 can define a first guide 105a and the top surface 152a of the actuator can define a second guide 105b that is complementary to the first guide 105a, such that the guides 105a and 105b can attach to each other so as to guide the actuator along the third direction D3. Similarly, the fourth end 103d of housing 103 can define a first guide 107a and a rear surface 154c of the electrical fuse conductor 154 can define a second guide 107b that is complementary to the first guide 107a, such that the guides 107a and 107b can attach to each other so as to guide the electrical fuse conductor along the first direction D1. The rear surface 154c can ride along the fourth end 103d of the housing when the electrical coil assembly is exposed to an MRI machine.

Referring also to FIG. 6A, the fuse element 150 can include the electrical fuse conductor 154 proximate to the electrical coil 104, and the fuse element 150 can be movable from a first or disengaged position 160 whereby the electrical fuse conductor 154 is spaced from at least two exposed regions of the electrical coil, to a second or engaged position 162 whereby the electrical fuse conductor 154 is in electrical communication with the at least two exposed regions, such that current flows from a first one of the two exposed regions through the electrical fuse conductor 154 to a second one of the two exposed regions. The exposed regions can be arranged as desired. For example, the front face 106a of the substrate can define one or more the exposed regions. In accordance with the illustrated embodiment, the first plurality of folded edges 118 can define one or more of the exposed regions. The electrical coil assembly 102 can be responsive to a magnetic field between approximately 1 Tesla and 5 Tesla so as to urge the fuse element 150 to move from the disengaged position 160 to the engaged position 162. In particular, the fuse element 150 can be responsive to a magnetic resonance imaging machine so as to move from the disengaged position 160 to the engaged position 162, wherein the engaged position 162 defines a short circuit.

In the engaged position 162, the electrical fuse conductor 154 can be in mechanical contact with at least two exposed regions, for instance at least two of the first plurality of folded edges 118, of the electrical coil 104. In an example, when the electrical fuse conductor 154 is in the engaged position 162, at least two of the first plurality of folded edges 118 are electrically coupled to one another via the electrical fuse conductor 154, for instance the bottom surface 154b of the electrical fuse conductor 154. The electrical coil assembly 102 can further include a bias element 156 configured to support the electrical fuse conductor 154, and thus the fuse element 150, in the disengaged position 160. The bias element 156 can include at least one spring element in contact with the electrical fuse conductor 154 so as to bias the electrical fuse conductor 154 along the first direction D1, though it will be understood that the fuse element 150 can be biased in an alternative direction or in alternative position as desired. In an example, the bias element 156 can be supported by a platform 176 that extends from the third end 103c of the housing 103. Thus, the bias element 156 can be supported by the housing 103, in particular the third end 103c of the housing 103. Further, it will be understood that the bias element 156 can be alternatively configured to bias the fuse element 150 in the disengaged position 160 or the engaged position 162.

In an alternative example embodiment, referring to FIG. 6B, the electrical fuse conductor 154 can be configured to be biased in the engaged position 162 in which the fuse element 150 is in contact with the electrical conductor of the electrical coil. The fuse element 150 can be movable from the engaged position 162 whereby the electrical fuse conductor 154 is in electrical communication with the electrical coil so as to electrically connect segments of the electrical coil with one another, to the disengaged position 160 whereby the electrical fuse conductor 154 is spaced from the electrical coil, such that the electrical coil defines a discontinuous electrical trace such that current does not flow through from the first end of the electrical coil to the second end of the electrical coil when the electrical fuse conductor is in the disengaged position 160. In accordance with the alternative example depicted in FIG. 6B, the electrical coil assembly 102 can be responsive to a magnetic field between approximately 1 Tesla and 5 Tesla so as to urge the fuse element 150 to move from the engaged position 162 to the disengaged position 160. In particular, the fuse element 150 can be responsive to a magnetic resonance imaging machine so as to move from the engaged position 162 to the disengaged position 160, wherein the disengaged position 160 defines an open circuit.

Referring in particular to FIG. 4, the actuator 152 can include, or can be composed of, at least one magnet configured to move along any direction as desired, for instance along the third direction D3, when the electrical coil assembly 102 is exposed to a magnetic field 158, which can be a static magnetic field induced by magnetic resonance imaging. Further, the electrical coil assembly 102 can include a plurality of actuators 152 (e.g., magnets), such that the actuators 152 are moveable in multiple directions, for instance the first direction D1, the second direction D2, and the third direction D3, to cause the electrical fuse conductor 154 to move toward (or away from) the electrical coil 104. Thus, the fuse element 150 can be moveable in response to magnetic fields having any direction. For example, in some cases, a patient having the electrical coil assembly 102 implanted may change orientation in an MRI machine, and because the actuators 152 can include an actuator positioned to respond to each direction of the magnetic field, the conductive fuse element 150 is urged toward the electrical coil 104 regardless of whether the patient changes orientation. Alternatively, or additionally, referring to FIG. 5, the electrical coil assembly 102 can further include a transfer member 170 having a first end 170a attached to a piezoelectric material 172. The transfer member can further include a second end 170b attached to the actuator 152. The piezoelectric material 172 can include a first terminal end 172a and a second terminal end 172b opposite the first terminal end 172a along the longitudinal direction. The first terminal end 172a can be attached to the third end 103c of the housing or can be otherwise prevented from moving or expanding toward the third end 103c. The second terminal end 172b can be attached to the first end 170a of the transfer member 170, such that, when the piezoelectric material expands, the second terminal end 172b of the piezoelectric material 172 and the electrical fuse conductor 154 do not move with respect to each other along the third direction D3.

The piezoelectric material 172 can configured to expand when the electrical coil assembly 102 is exposed to an electrical potential (voltage) that is induced within the electrical coil by a changing magnetic field produced by an MRI machine. The piezoelectric material 172 can reside within the plurality of holes 114. Alternatively, the piezoelectric material 172 can reside outside of the holes 114. In some cases, a ferromagnetic core can reside within some or all of the plurality of holes 114. In an example, the piezoelectric material 172 can extend through each of the plurality of segments 110. The piezoelectric material can include tourmaline, Rochelle sale, Quartz, or the like. In an example, regardless of whether the piezoelectric material resides inside or outside of the holes 114, the piezoelectric material 172 is electrically coupled to a first and second end of the electrical coil 104, such that when voltage is induced within the electrical coil 104 by magnetic resonance imaging, the piezoelectric material 172 expands, causing the electrical fuse conductor 154 to move, for instance toward the electrical coil 104. For example, the piezoelectric material 172 can be connected to the first end 116a supported by the first segment 110a, and the terminal end 116c of the conductor wire 116 supported by the rear segment 110b. In particular, the first terminal end 172a of the piezoelectric material can be electrically coupled to the first end 116a of the first segment, and the second terminal end 172b of the piezoelectric material 172 can be electrically coupled to the terminal end 116c. The piezoelectric material 172 can be arranged to expand along the third direction D3 when exposed to magnetic resonance imaging. In an example, the piezoelectric material 172 is configured to expand along the third direction D3 only toward the fourth end 103d of the housing 103 when exposed to magnetic resonance imaging. For instance, the piezoelectric material 172 can about the third end 103c of the housing 103 such that the piezoelectric material 172 cannot expand toward the third end 103c.

Referring now to FIG. 7, the electrical coil 104 can include the substrate 106 and an electrical conductor 108a defining a single continuous trace supported by the front face 106a of the substrate 106. The electrical coil 104 can be arranged in a folded position so as to define the first plurality of folded edges 118 and the second plurality of folded edges 120. In an example, the second plurality of folded edges 120 can include edges that are opposite folded edges in the first plurality of folded edges 118, for instance along the first direction D1. The electrical conductor 108a can define a first width 171 and a narrow location 173 having a second width 175 that is less than the first width 171, such that, when voltages or currents above a threshold are induced within the electrical coil 104, the electrical conductor 108a breaks at the narrow location 173 so as to no longer define the single continuous trace. The electrical conductor 108a can define one narrow location 173 or a plurality of narrow locations having the second width 175. For instance, adjacent segments 110 along the third direction D3 can define a pair of segments, and each pair of segments can support at least one narrow location 173 of the electrical conductor 108a. In an example, each pair of segments 110 supports only one narrow location 173 of the electrical conductor 108a. In another example, each segment 110 supports at least one, for instance one, narrow location 173 of the electrical conductor 108a.

In an example, a method of manufacturing the electrical coil assembly 102 includes stamping an electrical conductor on a first face of a substrate so as to define an electrical coil. The method can further include folding the electrical coil into a folded position so as to define a first plurality of folded edges of the electrical coil and a second plurality of folded edges opposite the first plurality of folded edges along a transverse direction. The method can further include arranging a fuse element proximate to the first plurality of folded edges, such that the fuse element is spaced from the first plurality of folded edges along the transverse direction, and such that the first face of the substrate faces the fuse element at the first plurality of folded edges, so as to expose the electrical conductor to the fuse element at the first plurality of folded edges.

In an example, the substrate defines a second face opposite the first face of the substrate, and the method of manufacturing the electrical coil assembly further includes stamping the electrical conductor only on the first face of the substrate. Folding the electrical coil into the folded position can include arranging the second face of the substrate to face inward at the first plurality of folded edges, and arranging the second face of the substrate to face outward at the second plurality of folded edges. The substrate can define a plurality of segments that each define an octagon, and folding the electrical coil into the folded position can include arranging the segments along a longitudinal direction substantially parallel to the transverse direction, such that each segment is attached to at least one other segment at a folded edge of the first or second plurality of folded edges. A method of manufacturing the electrical coil assembly can further include defining a plurality of holes in the substrate, and placing a piezoelectric material within the plurality of holes. Folding the electrical coil into the folded position can further include arranging the plurality of holes to align with one another along the longitudinal direction. In an example, stamping the electrical conductor includes stamping the electrical conductor about each hole so as to define a spiral pattern for each segment.

The method of manufacturing the electrical coil assembly can further include arranging the fuse element by configuring the electrical fuse conductor of the fuse element to move toward the first plurality of folded edges when the electrical coil assembly is exposed to a magnetic field. Arranging the fuse element can further include configuring the actuator to move along the longitudinal direction when the electrical coil assembly is exposed to the magnetic field, so as to cause the electrical fuse conductor to move toward the first plurality of folded edges. For example, the bottom surface of the actuator can be arranged to ride along the top surface of the electrical fuse conductor when the electrical coil assembly is exposed to a magnetic field or an electrical field. A method of manufacturing the electrical coil can further include selecting an electrically conductive material for the bottom surface of the electrical fuse conductor. Further, a bias element can be placed such that the bias element supports the electrical fuse conductor in a disengaged position in which the electrical fuse conductor is out of contact with the electrical conductor. The bias element can be configured to allow the electrical fuse conductor to move from the disengaged position to an engaged position in which the electrical fuse conductor contacts the electrical conductor at the first plurality of folded edges when pressure is applied to the bias element along the transverse direction. In an example, placing the bias element includes placing at least one spring element in contact with the electrical fuse conductor so as to bias the electrical fuse conductor along the transverse direction. The method of manufacture can also include electrically coupling the actuator to the first and second end of the electrical coil, such that when voltage is induced within the electrical coil by magnetic resonance imaging, the piezoelectric material with the holes expands, which can cause the actuator to move.

In operation, an electrical device or patient can be protected, using the electrical coil assembly, when the electrical device or patient is exposed to magnetic resonance imaging. The electrical device or patient can include an electrical coil comprising a substrate and an electrical conductor supported by a first face of the substrate. A method can include causing a fuse element including an electrical fuse conductor to move from a disengaged position in which the fuse element is spaced from at two exposed regions of the electrical coil to an engaged position in which the electrical fuse conductor is in electrical communication with the at least two exposed regions, such that current flows from a first one of the two exposed regions through the electrical fuse conductor to a second one of the at least two exposed regions. The method can further include causing the electrical fuse conductor of the fuse element to move toward the first plurality of folded edges along the transverse direction. The method can further include causing the actuator to move along a longitudinal direction that is substantially parallel to the transverse direction, so as to cause the electrical fuse conductor to move toward the first plurality of folded edges. The method can further include causing the bottom surface of the actuator to ride along the top surface of the electrical fuse conductor. Causing the fuse element to move from the disengaged position to the engaged position so as to define a short circuit can further include causing at least two of the first plurality of folded edges to be electrically coupled with one another via the fuse element. The method can further include returning the fuse element to the disengaged position from the engaged position, for example, when the electrical coil assembly is no longer exposed to an MRI machine. In an example, the method includes causing a piezoelectric material to expand, which can cause the electrical fuse conductor to move along the along the longitudinal direction.

In another example method, referring generally to FIG. 6B, the fuse element is caused, for instance by an MRI machine, to move from an engaged position whereby the electrical fuse conductor is in electrical communication with the electrical coil so as to electrically connect segments of the electrical coil with one another, to the disengaged position whereby the electrical fuse conductor is spaced from the electrical coil, such that the electrical coil defines an open circuit. When the electrical coil defines the open circuit, the electrical coil includes a discontinuous electrical trace such that current does not flow through from the first end of the electrical coil to the terminal end of the electrical coil when the electrical fuse conductor is in the disengaged position. In this configuration, the electrical coil assembly can be responsive to a magnetic field between approximately 1 Tesla and 5 Tesla so as to urge the fuse element to move from the engaged position to the disengaged position. In particular, the fuse element can be responsive to a magnetic resonance imaging machine so as to move from the engaged position to the disengaged position.

It will be appreciated by those skilled in the art that changes could be made to the embodiments described above without departing from the broad inventive concept thereof. Furthermore, it should be appreciated that the structure, features, and methods as described above with respect to any of the embodiments described herein can be incorporated into any of the other embodiments described herein unless otherwise indicated. It is understood, therefore, that this invention is not limited to the particular embodiments disclosed, but it is intended to cover modifications within the spirit and scope of the present disclosure. Further, it should be appreciated, that the term substantially indicates that certain directional components are not absolutely perpendicular to each other and that substantially perpendicular means that the direction has a primary directional component that is perpendicular to another direction.

What is claimed:

1. An electrical coil assembly, comprising:
   an electrical coil including a substrate and an electrical conductor supported by the substrate, the electrical coil defining at least two exposed regions; and
   a fuse element including an electrical fuse conductor proximate to the electrical coil, the fuse element movable from a disengaged position whereby the electrical fuse conductor is spaced from the at least two exposed regions, to an engaged position whereby the electrical fuse conductor is in electrical communication with the at least two exposed regions, such that current flows from a first one of the two exposed regions through the electrical fuse conductor to a second one of the two exposed regions,
   wherein the electrical coil assembly is responsive to a magnetic field between approximately 1 Tesla and 5 Tesla so as to urge the fuse element to move from the disengaged position to the engaged position,
   wherein the fuse element further includes an actuator adjacent to the electrical fuse conductor, the actuator moveable so as to cause the electrical fuse conductor to move toward the at least two exposed regions, and
   wherein the actuator defines a top surface and a bottom surface opposite the top surface, and the electrical fuse conductor defines a top surface and a bottom surface opposite the top surface, and the bottom surface of the actuator is configured to ride along the top surface of the electrical fuse conductor when the electrical coil assembly is exposed to the magnetic field.

2. The electrical coil assembly as recited in claim 1, wherein the fuse element is movable to the engaged position whereby the electrical fuse conductor is in mechanical contact with the at least two exposed regions.

3. The electrical coil assembly as recited in claim 1, wherein the fuse element is responsive to a magnetic resonance imaging machine so as to move from the disengaged position to the engaged position.

4. The electrical coil assembly as recited in claim 1, wherein the electrical conductor is supported by a first face of the substrate, and the electrical coil is arranged in a folded position so as to define a first plurality of folded edges defining the at least two exposed regions.

5. The electrical coil assembly as recited in claim 4, wherein, when the electrical fuse conductor is in the engaged position, at least two of the first plurality of folded edges are electrically coupled to one another via the electrical fuse conductor.

6. The electrical coil assembly as recited in claim 1, wherein the bottom surface of the electrical fuse conductor comprises electrically conductive material.

7. The electrical coil assembly as recited claim 1, the electrical coil assembly further comprising a bias element that supports the electrical fuse conductor in the disengaged position.

8. The electrical coil assembly as recited in claim 7, wherein the bias element comprises at least one spring element in contact with the electrical fuse conductor so as to bias the electrical fuse conductor in the disengaged position.

9. An electrical coil assembly, comprising:
   an electrical coil including a substrate and an electrical conductor supported by the substrate, the electrical coil defining at least two exposed regions; and
   a fuse element including an electrical fuse conductor proximate to the electrical coil, the fuse element movable from a disengaged position whereby the electrical fuse conductor is spaced from the at least two exposed regions, to an engaged position whereby the electrical fuse conductor is in electrical communication with the at least two exposed regions, such that current flows from a first one of the two exposed regions through the electrical fuse conductor to a second one of the two exposed regions,
   wherein the electrical coil assembly is responsive to a magnetic field between approximately 1 Tesla and 5 Tesla so as to urge the fuse element to move from the disengaged position to the engaged position,
   wherein the fuse element further includes an actuator adjacent to the electrical fuse conductor, the actuator moveable so as to cause the electrical fuse conductor to move toward the at least two exposed regions, and
   wherein the actuator is configured to move along a longitudinal direction when the electrical coil assembly is exposed to the magnetic field, so as to cause the electrical fuse conductor to move along a transverse direction that is substantially perpendicular to the longitudinal direction.

10. The electrical coil assembly as recited in claim 9, the actuator comprising a magnet movable along the longitudinal direction when the electrical coil assembly is exposed to the magnetic field.

11. The electrical coil assembly as recited in claim 9, wherein the actuator is attached to a piezoelectric material configured to expand when the electrical coil assembly is exposed to the magnetic field.

12. The electrical coil assembly as recited in any of claim 11, wherein the piezoelectric material is electrically coupled to a first and second end of the electrical coil, such that when voltage is induced within the electrical coil by the magnetic field, the piezoelectric material expands along the longitudinal direction.

13. The electrical coil assembly as recited in claim 9, wherein the actuator defines a top surface and a bottom surface opposite the top surface, and the electrical fuse conductor defines a top surface and a bottom surface opposite the top surface, and the bottom surface of the actuator is configured to ride along the top surface of the electrical fuse conductor when the electrical coil assembly is exposed to the magnetic field.

14. The electrical coil assembly as recited in claim 13, wherein the bottom surface of the electrical fuse conductor comprises electrically conductive material.

\* \* \* \* \*